US007132554B2

(12) United States Patent
Rose

(10) Patent No.: US 7,132,554 B2
(45) Date of Patent: Nov. 7, 2006

(54) THERAPEUTIC SYNERGY OF ANTI-CANCER COMPOUNDS

(75) Inventor: William C. Rose, Pipersville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 14 days.

(21) Appl. No.: 11/079,064

(22) Filed: Mar. 14, 2005

(65) Prior Publication Data
US 2005/0244407 A1 Nov. 3, 2005

Related U.S. Application Data

(60) Provisional application No. 60/553,505, filed on Mar. 16, 2004.

(51) Int. Cl.
A61K 31/337 (2006.01)
C07D 305/14 (2006.01)

(52) U.S. Cl. .................. 549/510; 549/200; 514/449

(58) Field of Classification Search .......... 530/388.22, 530/387.3, 388.1, 387.7; 514/449; 549/510, 549/200
See application file for complete search history.

(56) References Cited

U.S. PATENT DOCUMENTS

| 4,943,533 | A | 7/1990 | Mendelsohn et al. |
| 5,558,864 | A | 9/1996 | Bendig et al. |
| 5,705,508 | A | 1/1998 | Ojima et al. |
| 5,891,996 | A | 4/1999 | Mateo de Acosta del Rio et al. |
| 6,235,883 | B1 * | 5/2001 | Jakobovits et al. .... 530/388.22 |
| 6,750,246 | B1 | 6/2004 | Kadow et al. |

FOREIGN PATENT DOCUMENTS

| WO | WO 01/27115 | 4/2001 |
| WO | WO 01/57027 | 8/2001 |

OTHER PUBLICATIONS

Cecil, Textbook of Medicine, 21st Edition (2000), Goldman & Bennett (Editors), W.B. Saunders Company (Publisher), Chapter 198, pp. 1060-1074.*
Tortora G, et al., "Cooperative inhibitory effect of novel mixed backbone oligonucleotide targeting protein kinase A in combination with docetaxel... breast cancer cell growth", Clin. Cancer Res. Apr. 1999; 5(4):875-81.*
Inoue K, et al. "Paclitaxel enhances the effects of the anti-epidermal growth factor receptor monoclonal antibody ImClone C225 in mice with metastatic human bladder transitional cell carcinoma," Clin Cancer Res Dec. 2000; 6(12): 4874-84.*

(Continued)

Primary Examiner—Ardin H. Marschel
Assistant Examiner—Amy Lewis
(74) Attorney, Agent, or Firm—Elliot Korsen

(57) ABSTRACT

This invention relates to a synergistic therapeutic combination of anti-cancer compounds which comprises a) a taxane, and b) a substance that binds to the epidermal growth factor receptor (EGFR) and blocks the ability of epidermal growth factor (EGF) to intitiate receptor activities which results in tumor growth inhibition, and optionally at least one pharmaceutically acceptable carrier for simultaneous, separate or sequential use.

9 Claims, 2 Drawing Sheets

OTHER PUBLICATIONS

Karashima T, et al., "Inhibition of angiogenesis by the antiepidermal growth factor receptor antibody C225 . . . ," May 2002 Clin Cancer Research vol. 8, 1253-1264.*

Cassinelli G, et al., "Cellular bases of the antitumor activity of the novel taxane IDN 5109 (BAY59-8862) on hormone-refractory prostate cancer," 2002 Clin Cancer Research vol. 8: pp. 2647-2654.*

Shionoya M et al., "DJ-927, a novel oral taxane, overcomes p-glycoprotein-mediated multidrug resistance in vitro and in vivo," May 2003 Cancer Sci vol. 94(5): 459-466.*

Sampath D et al., "MAC-321, a novel taxane with greater efficacy than paclitaxel and docetaxel in vitro and in vivo," Sep. 2003 Mol Cancer Ther vol. 2: 873-884.*

Ciardiello F and Tortora G, "Anti-epidermal growth factor receptor drugs in cancer therapy," Expert Opinion Investig. Drugs 2002 vol. 11(6): 755-768.*

Rose, W.C. et al., "Therapeutic Synergy of Oral Taxane BMS-275183 and Cetuximab *versus* Human Tumor Xenografts", Clinical Cancer Research, vol. 10, pp. 7413-7417 (2004).

U.S. Appl. No. 60/680,691, filed May 13, 2005, Voi et al.

* cited by examiner

THERAPEUTIC SYNERGY OF ANTI-CANCER COMPOUNDS

This application claims the priority benefit of U.S. Provisional application No. 60/553,505 filed on Mar. 16, 2004, which is incorporated herein by reference in its entirety.

FIELD OF THE INVENTION

This invention relates to a synergistic combination of anti-cancer compounds which comprises a) a taxane, and b) an epidermal growth factor receptor (EGFR) antibody, and optionally at least one pharmaceutically acceptable carrier for simultaneous, separate or sequential use.

BACKGROUND OF THE INVENTION

The taxanes are best known by the first two marketed representatives of this chemical class, Taxol® and Taxotere®. Neither drug is orally bioavailable without being co-administered with some facilitating agent or processed into nanoparticles. Bristol Myers-Squibb has a compound which is the first of several orally active taxanes to enter clinical trial. It has been found in Phase I testing to have notable activity in heavily pretreated patients with non-small cell lung cancer (NSCLC), including those pretreated with Taxotere® and/or Iressa® (gefitinib), a small molecule anti-epidermal growth factor receptor (EGFR) inhibitor.

EGFR antibodies can be selected from chimerized, humanized, fully human, and single chain antibodies derived from the murine antibody 225 described in U.S. Pat. No. 4,943,533 to Mendelsohn et al. The EGFR antibody can be, for example, cetuximab which is marketed as Erbitux™ by ImClone Systems, Inc. and Bristol-Myers Squibb Company. The EGFR antibody can also be selected from the antibodies described in U.S. Pat. No. 6,235,883 to Jakobovits et al., U.S. Pat. No. 5,558,864 to Bendi et al., and U.S. Pat. No. 5,891,996 to Mateo de Acosta del Rio et al.

SUMMARY OF THE INVENTION

This invention relates to a synergistic combination of anti-cancer compounds which comprises a) a taxane, and b) an EGFR antibody, and optionally at least one pharmaceutically acceptable carrier for simultaneous, separate or sequential use.

In particular, it has been found that oral taxane compounds, when administered essentially simultaneously with an epidermal growth factor receptor antibody, exhibited therapeutically synergistic antitumor activity in human tumor xenograft models.

More particularly, it has been found that oral taxane compounds, when administered essentially simultaneously with the epidermal growth factor receptor antibody, cetuximab, exhibited therapeutically synergistic antitumor activity in human tumor xenograft models.

DETAILED DESCRIPTION OF THE INVENTION

Figure 1:
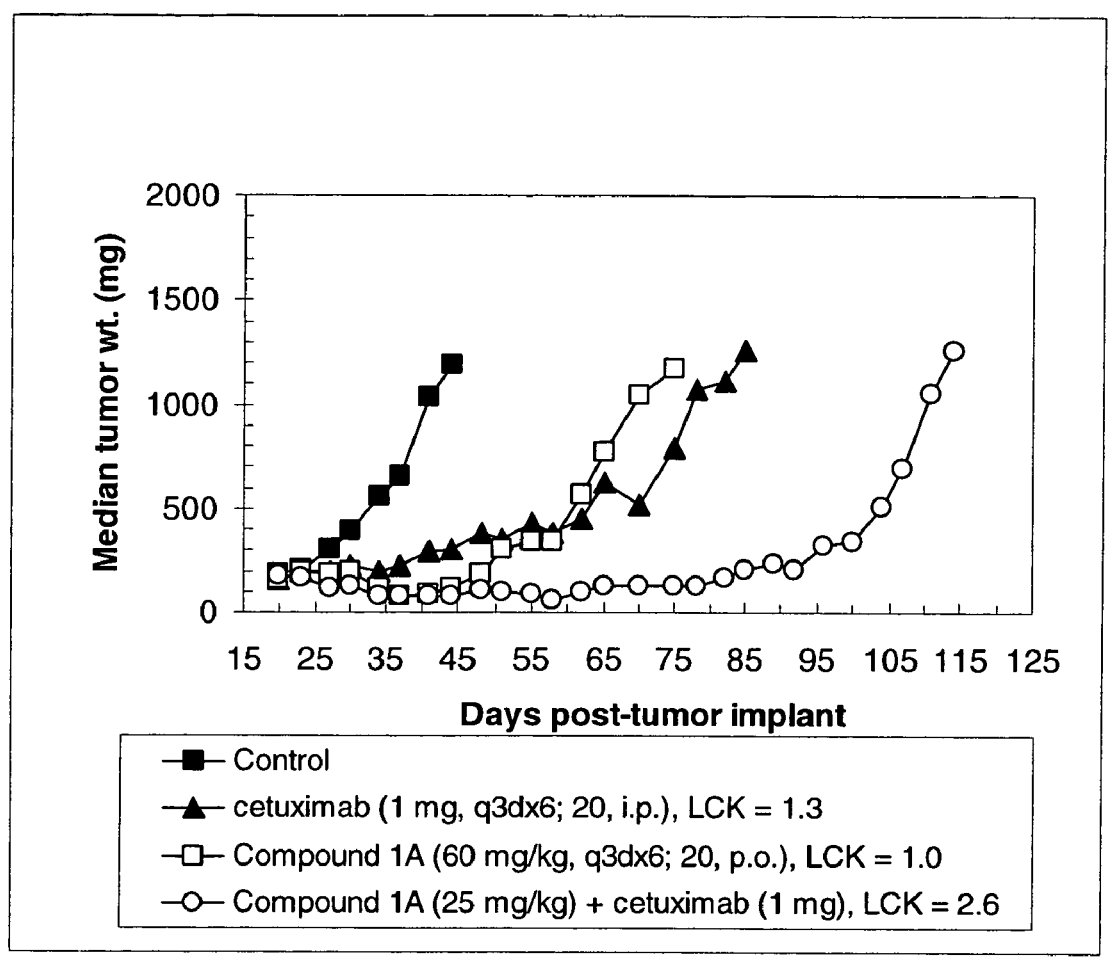
FIG. 1. Synergistic combined modality therapy using an oral taxane, Compound Ia, plus the EGFR antibody, cetuximab, versus the human L2987 lung carcinoma xenograft. Optimal regimens for each therapy evaluated, and their associated log cell kill (LCK) effects, are shown in the legend.

It has been found that certain oral taxane compounds, when administered either simultaneously or sequentially with an EGFR antibody, exhibit therapeutically synergistic antitumor activity in human tumor xenograft models. The invention also relates to methods of treating cancer and other proliferative diseases using the synergistic therapeutic combination of compounds.

Oral taxane compounds of the formula

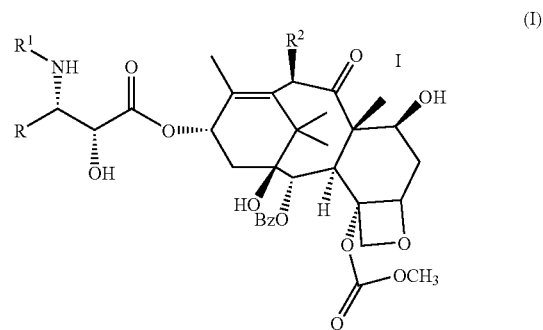

wherein:

R is phenyl, isopropyl, or tert butyl;

$R^1$ is —C(O)$R^z$ in which $R^z$ is $(CH_3)_3CO$—, $(CH_3)_3CCH_2$—, $CH_3(CH_2$cyclobutyl-, cyclohexyloxy, or (2-furyl);

$R^2$ is $CH_3C(O)O$—;

or pharmaceutically acceptable salts, solvates, esters or isomers thereof, are used in the combination and methods of the invention. These compounds and their preparation are disclosed in U.S. Ser. No. 09/712,352, filed Nov. 14, 2000, the disclosure of which is incorporated herein by reference.

Additional oral taxanes may be useful in the synergistic combinations of the invention. These include the following:

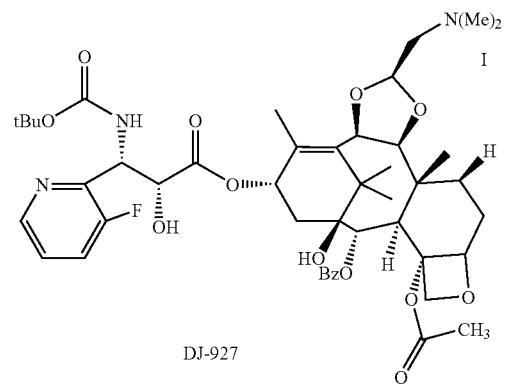

DJ-927

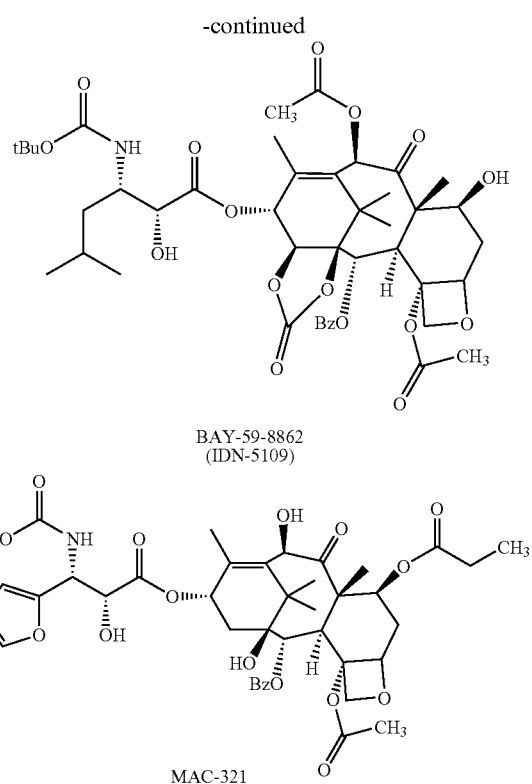

BAY-59-8862
(IDN-5109)

MAC-321

DJ-927 and its synthesis is disclosed in WO 01/27115, the disclosure of which is incorporated herein in its entirety. IDN-5109 (BAY59-8862) and its synthesis is disclosed in U.S. Pat. No. 5,705,508, the disclosure of which is incorporated herein in its entirety. MAC-321 and its synthesis is disclosed in WO 2001057027, the disclosure of which is incorporated herein in its entirety.

A particular oral taxane of the formula

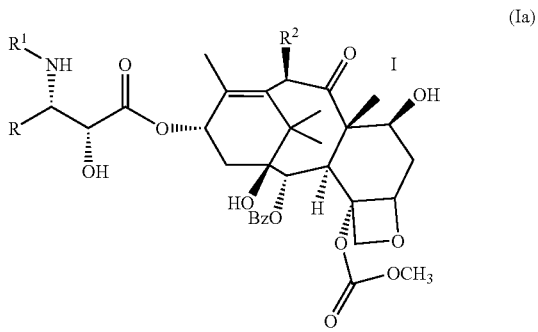

(Ia)

wherein:

R is tert butyl;

$R^1$ is —C(O)$R^z$ in which $R^z$ is $(CH_3)_3CO$—; and $R^2$ is $CH_3C(O)O$—, or a pharmaceutically acceptable salt thereof, is also disclosed.

The EGFR antibodies can be selected from chimerized, humanized, fully human, and single chain antibodies derived from the murine antibody 225 described in U.S. Pat. No. 4,943,533 to Mendelsohn et al. The EGFR antibody can be, for example, cetuximab which is marketed as Erbitux™ by ImClone Systems, Inc. and Bristol-Myers Squibb Company. The EGFR antibody may also be selected from the antibodies described in U.S. Pat. No. 6,235,883 to Jakobovits et al., U.S. Pat. No. 5,558,864 to Bendi et al., and U.S. Pat. No. 5,891,996 to Mateo de Acosta del Rio et al.

The EGFR monoclonal antibody, Erbitux® (cetuximab) was found to provide the therapeutically synergistic antitumor activity in vivo when combined with the oral taxane.

The nature of proliferative diseases like solid tumor diseases is multifactorial. Under certain circumstances, drugs with different mechanisms of action may be combined. However, just considering any combination of drugs having different modes of action does not necessarily lead to combinations with advantageous effects. In fact, drugs within the same class may not all have the same effect when used in combination.

It has been surprisingly found that the combination of the oral taxane of formula Ia plus EGFR monoclonal antibody, cetuximab, provided therapeutically synergistic antitumor activity in two different human tumor xenograft models. Synergies were observed at doses below maximum tolerated dose (MTD) levels, but the combination was tolerated even at doses combining solo drug MTD or optimal dose levels.

It can be shown by established test models and in particular those models described herein that the combination of the invention results in synergistic activity compared to the effects observed with the single combination partners. The pharmacological activity of the combination of the invention may be further demonstrated in a clinical study as well as in the procedure described herein.

In one embodiment of the invention, each patient receives an EGFR antibody, such as cetuximab, on a weekly or other clinically useful schedule, at dose levels typically used for the particular EGFR antibody involved. In the specific instance of cetuximab, that might include an initial dose of 400 mg/m$^2$ followed thereafter by 250 mg/m$^2$ weekly, or a regimen of similar dose levels adjusted for optimal use in the combination setting. The oral taxane, Compound Ia, could be administered on any clinically useful schedule, including, but not limited to, daily, twice weekly, weekly or every other week. Specifically, for weekly administration, typical dosages of Compound Ia might range from 50 to 320 mg/m$^2$, adjusted as the clinician saw fit, to accommodate any developing patient needs.

In another embodiment, Compound Ia is administered orally at a synergistically thereapeutic effective dose of 8 to 320 mg/m$^2$ p.o. every 1 to 14 days for 1 or more administrations and cetuximab is administered at a synergistically thereapeutic effective dose of 4 to 400 mg/m$^2$. i.v. every 1 to 14 days for 1 or more administrations.

Therapeutic synergy represents a therapeutic effect achieved with a tolerated regimen of a combination treatment that exceeds the optimal effect achieved at any tolerated dose of monotherapy associated with the same drugs used in the combination.

The following are definitions of terms that may be used in the present specification. The initial definition provided for a group or term herein applies to that group or term throughout the present specification individually or as part of another group, unless otherwise indicated.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention includes all the possible stereoisomers and their mixtures. Particularly preferred are the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Any compound that will be converted in vivo to provide the bioactive agent (i.e., the compound for formulas I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991); and c) H. Bundgaard, *Advanced Drug Delivery Reviews*, 8, 1–38 (1992).

It should further be understood that solvates (e.g., hydrates) of the compounds of formula I are also with the scope of the present invention. Methods of solvation are generally known in the art.

The combination of the invention is useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkitt's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The following abbreviations used are: anti-EGFR, anti-epidermal growth factor receptor; MTD, maximum tolerated dose; OD, optimal dose; LCK, gross $\log_{10}$ cell kill; mg/kg/adm, milligrams/kilogram/administration; NSCLC, non-small cell lung cancer; T, drug-treated group; C, control group, g, grams; ml, milliliter; q, every.

EXAMPLES

Materials and Methods

Compounds. The oral taxane (Ia) was synthesized by Bristol-Myers Squibb (BMS) chemists. The compound was dissolved initially in equal portions of Cremophor EL and ethanol, followed by aqueous dilution to yield final ethanol and Cremophor EL concentrations of 10%. Cetuximab (also known as Erbitux®) was a gift of Imclone Systems, Inc. The antibody was dissolved in phosphate buffered saline for i.p. injection to mice The oral taxane was administered to mice in a volume of 0.01 ml/g of body weight based on the average weight of the mice in each group at the time of treatment. Cetuximab was administered in 0.25 ml on a per mouse basis.

Animals. Athymic ("nude") mice, 5–6 weeks of age, purchased from Harlan Sprague Dawley (Indianapolis, Ind.), were quarantined for ~2 weeks before their use for tumor propagation and drug efficacy testing. They were fed food and water ad libitum. All studies involving these animals were conducted in accordance with NIH (Bethesda, Md.) and Bristol Myers-Squibb animal care and use guidelines.

Tumors. Human L2987 lung and GEO colon carcinomas were maintained in nude mice by serial s.c. passage. All efficacy testing involved tumors implanted s.c. in nude mice. Treatment was initiated when tumors had become well established at between 100–200 mg.

Antitumor Testing. A detailed description of the methods used to assess antitumor effects has been provided previously in Rose, W. C., Fairchild, C., and Lee, F. Y. F. Preclinical antitumor activity of two novel taxanes. Cancer Chemother. Pharmacol. 47: 97–105, 2001. Briefly, therapeutic results are presented in terms of either cures and/or primary tumor growth inhibition determined by calculating the relative median times for drug-treated (T) and control (C) groups of mice to grow tumors of 1 g target size, and expressed as T-C values (in days). Delays in tumor growth are also converted to log cell kill (LCK) values by methods described in the same article. Statistical evaluations of data were performed using Gehan's generalized Wilcoxon test for comparisons of time to reach tumor target size. Statistical significance was declared at $P<0.05$. Group sizes typically consisted of eight mice. Activity was defined as $\geq 1$ LCK.

Definitions of MTD and OD have been published previously in the above-noted article. Therapeutic results were reported at the OD, i.e., that yielding the best effect without exceeding the MTD. Therapeutic synergy represents a therapeutic effect achieved with a tolerated regimen of a combination treatment that exceeds the optimal effect achieved at any tolerated dose of monotherapy associated with the same drugs used in the combination. Cured mice are defined as those whose tumors are $\leq 35$ mg when assessed 10 tumor volume doubling times (based on control tumor growth between 500 mg and 1 g) post-termination of treatment. A regimen was described as "toxic" if more than one mouse died during or within 10 days following the final drug treatment, or anytime after the initiation of drug therapy whose tumor size at the time of death was below 1 g.

When Compound Ia and cetuximab were both administered to mice, they were given essentially simultaneously, with no attempt at any particular sequence applied.

Results

L2987 Human Lung Carcinoma. In the first of two experiments, Compound Ia was administered p.o. to mice bearing established L2987 tumors. The highest dose administered, 60 mg/kg/adm, every third day for 4 administrations (i.e., q3dx4) was tolerated and did not challenge the historical MTD of approximately 300 mg/kg cumulative exposure established using a similar schedule. The treatment produced 0.6 LCK, an effect not quite in the active range. Cetuximab administered at 1 mg/mouse, i.p., q3dx4, was well tolerated and produced 0.6 LCK, similar to the borderline effect achieved using the oral taxane. The results of this pilot study, as well as the combination treatment data to be described, are summarized below in Table 1.

TABLE 1

Combination Therapy Of Oral Taxane Compound Ia with EGFr Inhibitor versus Human L2987 Lung Carcinoma Xenografts: Highlights of Two Experiments

| Treatment[1] | | Average body weight change, g[2] (dead/total) | T-C (days)[3] | LCK (cures/total)[4] |
|---|---|---|---|---|
| Compound Ia | Cetuximab | | | |
| Pilot Study | | | | |
| 60 | — | 1.0 | 14.0 | 0.6 |
| 40 | — | 0.7 | 5.5 | 0.2 |
| — | 1 | 1.1 | 14.3 | 0.6 |
| 40 | 1 | 0.9 | 43.0 | 1.9 (2/8)[5] |
| 25 | 1 | 2.7 | 31.0 | 1.3 |
| Confirmatory Study | | | | |
| 60 | — | −0.9 | 28.0 | 1.0 |
| 40 | — | 1.5 | 14.5 | 0.5 |
| — | 1 | 1.3 | 36.5 | 1.3 |
| 40 | 1 | 1.2 | 57.8 | 2.0 (1/8) |
| 25 | 1 | 1.1 | 71.0 | 2.6 (3/8)[5] |

[1]In mg/kg/adm, p.o., for Compound Ia and mg/mouse, i.p. for cetuximab. In the pilot study, Compound Ia and cetuximab were administered q3dx4. All treatments began on Day 22 post-tumor implant. In the confirmatory study, Compound Ia and cetuximab were given q3dx6, with all treatments begun on Day 20 post-tumor implant. Treatment resulting in more than one death is described as "TOX" (i.e., toxic).
[2]Determined from beginning to end of treatment period. Controls gained 2.0 g in the pilot study and 1.8 g in the confirmatory study. If any mice died during therapy, or within 10 days following the end of therapy, the incidence is shown in parentheses.
[3]T-C values are based on relative median times (in days) for treated (T) and control (C) mice to reach tumors of 1.0 g.
[4]Log Cell Kill (LCK), and cures/total, if any, the definitions of which are explained in the Materials and Methods section.
[5]P < 0.01 versus best monotherapy.

A dramatic therapeutic enhancement was observed using the combination of oral taxane plus cetuximab. Whereas each highest dose monotherapy was associated with 0.6 LCK, combinations of 1 mg/mouse of cetuximab with either 25 or 40 mg/kg/adm of the oral taxane yielded 1.3 and 1.9 LCK, respectively. The latter combination also produced 2 of 8 mice cured and was significantly better (P<0.01) than the best monotherapies evaluated. Additionally, there was no body weight loss associated with the combination therapy.

In the confirmatory experiment, the same combinations of oral taxane plus cetuximab was evaluated on the same intermittent administration schedule, but a more protracted treatment regimen, q3dx6, was used to achieve clear monotherapy and combination MTD levels, and to evaluate and simulate the more protracted, chronic applications envisioned clinically. A cumulative exposure of 360 mg/kg (60 mg/kg/adm, q3dx6) of Compound Ia was tolerated with minimal body weight loss, but represents an MTD. A summary of the optimal effects of both monotherapies and combination treatments is also shown in Table 1.

Cetuximab monotherapy produced 1.3 LCK, a better result than in the pilot study and expected given the extended treatment regimen applied and the tolerability of the therapy. Combinations of oral taxane plus cetuximab produced enhanced delays in tumor growth compared to either optimal monotherapy of its component drugs. The best combination regimen evaluated involved 1 mg/mouse/adm of cetuximab with 25 mg/kg/adm of oral taxane, representing 2.6 LCK with 3 of 8 mice cured. Combinations containing higher doses of oral taxane were also well tolerated, but provided no greater activity than the effect just described (an inexplicable inversion in anticipated dose-response). The advantage of this particular combination regimen over the optimal monotherapies is illustrated in FIG. 1. The synergies produced using Compound Ia with cetuximab were not accompanied by enhanced toxicity as reflected by severe body weight loss, but rather showed no enhanced weight loss whatsoever compared to comparable monotherapy.

GEO human colon carcinoma. The protracted schedules of treatments used in the second L2987 experiment were applied to our one study using the GEO tumor model. Established GEO tumors were moderately sensitive to cetuximab, reflected by a borderline active 0.7 LCK following treatment with 1 mg/mouse/adm, i.p., q3dx6, beginning on Day 11 post-tumor implant. There was no body weight loss associated with the therapy. The oral taxane, Compound Ia, was only capable of producing a borderline active effect of 0.7 LCK at its MTD, 60 mg/kg/adm, p.o., q3dx6. These results, and the effects of selected combination therapies applied to mice bearing GEO tumors, are summarized below in Table 2.

TABLE 2

Combination Therapy Of Oral Taxane Compound Ia with EGFr Inhibitors versus Human GEO Colon Carcinoma Xenografts

| Treatment[1] | | Average body weight change, g[2] (dead/total) | T-C (days)[3] | LCK[4] |
|---|---|---|---|---|
| Compound Ia | Cetuximab | | | |
| 90 | — | (3/8) | TOX | TOX |
| 60 | — | −1.8 | 10.0 | 0.7 |
| 40 | — | −2.6 | 4.0 | 0.3 |
| — | 1 | 1.4 | 10.0 | 0.7 |
| 60 | 1 | −2.5 | 27.8 | 1.9[5] |
| 40 | 1 | 0 | 15.5 | 1.0 |

[1]In mg/kg/adm, p.o., for Compound Ia, and mg/mouse, i.p. for cetuximab. Compound Ia and cetuximab were administered q3dx6. All treatments began on Day 11 post-tumor implant
[2-4]See footnotes 2–4 in Table 1. The same information applies to the relevant item in Table 2. Control mice gained 0.2 g. There were no cures in any group.
[5]P < 0.001 versus best monotherapy.

Figure 2:
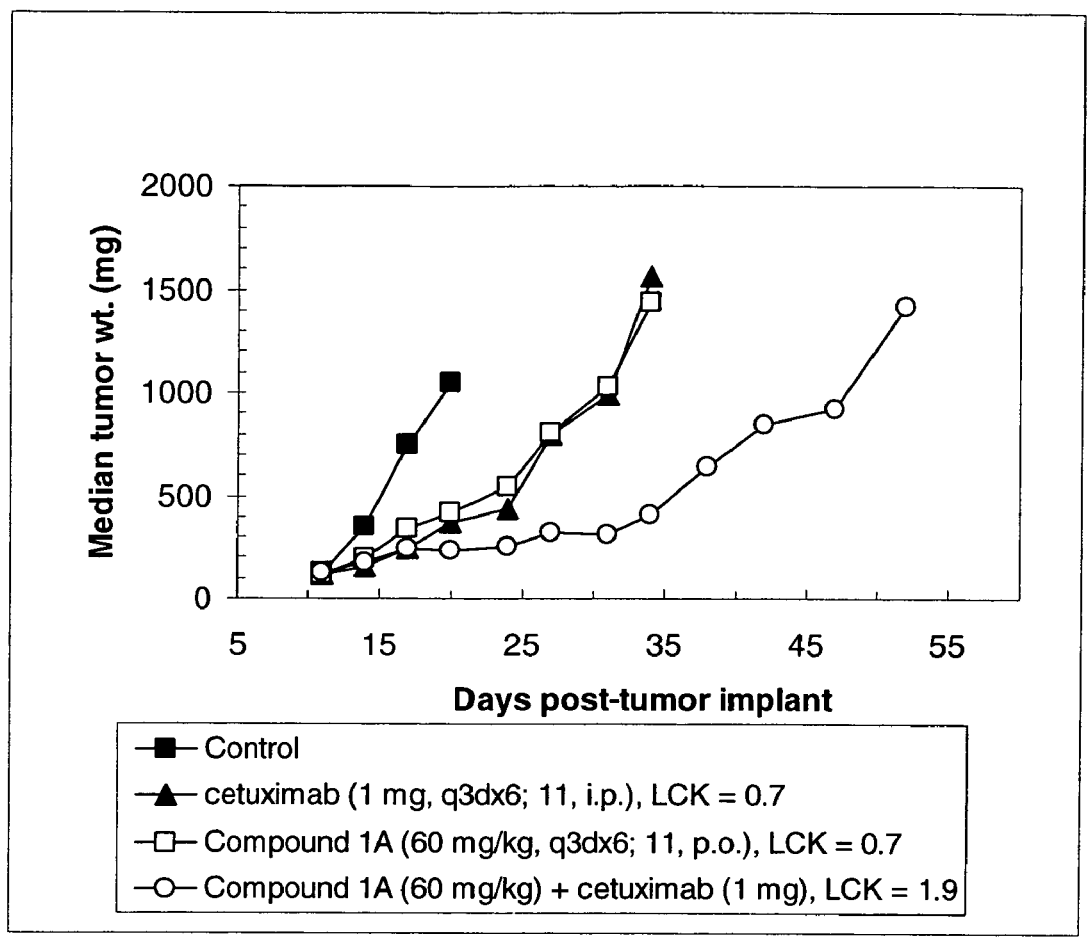
FIG. 2. Synergistic combined modality therapy using oral taxane, Compound Ia, plus the EGFR antibody, cetuximab, versus the human GEO colon carcinoma xenograft. Optimal regimens for each therapy evaluated, and their associated LCK effects, are shown in the legend.

Combination therapies were evaluated using the GEO carcinoma in an attempt to extend the observation of therapeutic synergy achieved with cetuximab plus oral taxane in the L2987 lung carcinoma. A combination of 60 mg/kg/adm of oral taxane plus 1 mg/mouse of cetuximab produced a therapeutically synergistic 1.9 LCK which was statistically different (P<0.001) than either optimal monotherapy, and with associated body weight loss no worse than seen using Compound Ia alone. The advantage of this combination over optimal monotherapies is illustrated in FIG. 2.

Parenteral administration of drugs is not conducive to protracted, repetitive, chronic treatment applications. The recent advent of weekly regimens for the delivery of taxanes clinically, and the apparent success associated with their deployment in this manner, provides an impetus for the development of oral versions with at least comparable efficacy and no worse a toxicologic profile. With the availability of a clinically active oral taxane, a wide range of different schedule options becomes feasible.

The preclinical activity of Compound Ia was observed using several different schedules, with an intermittent administration regimen being optimal in one carefully examined tumor model. The oral taxane also has shown activity and manageable toxicity in a phase I clinical trial using a weekly schedule of administration. Heavily pretreated patients, typically having received two or three prior chemo/radiotherapies, have responded to weekly Compound Ia. All but one of the several responding patients had NSCLC, and all but one of these had previously received either a parenteral taxane or a small molecule anti-EGFR compound, gefitinib, or both. The purpose of our current investigations was to evaluate this oral taxane versus preclinical human tumor models using a multiple administration treatment regimen, in combination with an inhibitor of EGFR.

The EGFr antibody selected for this study was the chimeric monoclonal antibody, cetuximab. Cetuximab has recently been approved in the United States for the treatment of colon cancer.

The L2987 human lung carcinoma has been characterized as positive for the EGF receptor and borderline levels of antitumor activity for cetuximab have been described. The GEO human colon carcinoma is also known to be EGF receptor positive and amongst the responsive tumor models to cetuximab and gefitinib, a small molecule anti-EGFR inhibitor.

Using the L2987 lung tumor xenograft, it was found that there was no increase in toxicity when combining Compound Ia with cetuximab. Essentially full doses, i.e., the biologically optimal dose or MTD of each therapeutic, could be administered in combination without causing unexpected body weight loss or deaths. Against the human L2987 lung carcinoma model, neither the oral taxane nor cetuximab at optimal dose levels was associated with more than modest, borderline antitumor activity when given as a solo therapy. Yet the combination of these two agents yielded a therapeutically synergistic outcome. Improvements of greater than 1 LCK beyond the therapeutic potential of either solo treatment were observed in confirmatory L2987 experiments, resulting even in the cure of several mice. The finding of therapeutic synergy for the oral taxane plus cetuximab was further confirmed in the GEO tumor model. Unlike claims for synergy often described for agents when a combination produces greater activity than either solo agent used at the same dose found in the combination, the oral taxane plus cetuximab therapeutic synergy is one whose combination effects are superior to those produced by the optimal tolerable dose of either component used alone.

Inoue et al., Clin. Canc. Res. 6:4874–4884, 2000, have described the combined use of paclitaxel with cetuximab in a transitional cell bladder carcinoma orthotopically-implanted in nude mice. Combination therapy with both drugs resulted in significantly greater regression of tumors compared with either agent alone. These investigators concluded that therapy with paclitaxel increased the ability of cetuximab to inhibit tumorigenicity and metastases possibly caused by inhibition of angiogenesis and induction of apoptosis. We have not investigated the possible mechanisms responsible for the observed synergy between the oral taxane and cetuximab in our antitumor studies.

Despite advances in the past decade, patients with NSCLC and other tumors are in need of more effective therapeutic interventions. The preclinical data presented here, demonstrating a dramatic therapeutic synergy when the oral taxane, Compound Ia, and EGFR antibody, cetuximab, were combined in the treatment of two human tumor xenografts, suggest an approach that ought to be evaluated clinically in appropriate indications.

I claim:

1. A synergistic pharmaceutical combination of anticancer compounds which comprises
   a) an orally administered taxane compound of the formula,

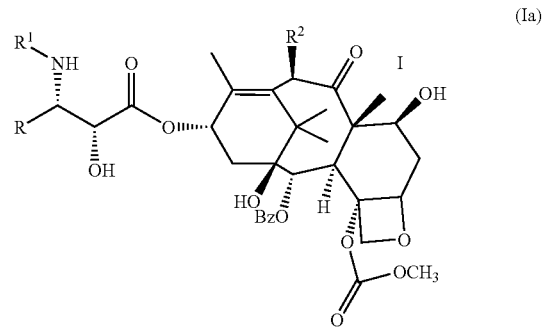

(Ia)

wherein:
R is ted butyl;
$R^1$ is —C(O)$R^Z$ in which $R^Z$ is $(CH_3)_3CO$—; and
$R^2$ is $CH_3C(O)O$—, and b) the epidermal growth factor receptor antibody, cetuximab, in which the active ingredients are present in each case in free form or as a pharmaceutically acceptable salt, solvate or ester.

2. The combination according to claim 1 wherein the taxane is administered orally at a synergistically thereapeutic effective dose of 8 to 320 mg/m² p.o. every 1 to 14 days for 1 or more administrations.

3. The combination according to claim 1 wherein cetuximab is administered at a synergistically thereapeutic effective dose of 4 to 400 mg/m². i.v. every 1 to 14 days for 1 or more administrations.

4. The combination according to claim 1 wherein the taxane is administered orally at at a synergistically thereapeutic effective dose of 8 to 320 mg/² p.o. every 1 to 14 days for 1 or more administrations and cetuximab is administered at a synergistically thereapeutic effective dose of 4 to 400 mg/m². i.v. every 1 to 14 days for 1 or more administrations.

5. A method for the treatment of cancer which comprises administering to a patient in need thereof a synergistically therapeutic amount of
   a) an orally administered taxane compound of the formula,

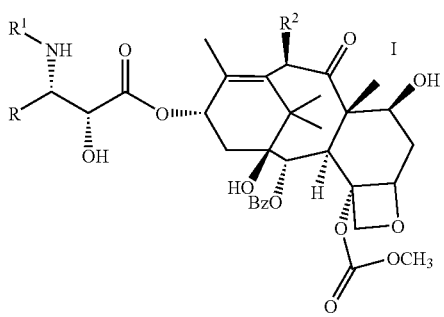

wherein:
R is ted butyl;
$R^1$ is —C(O)$R^Z$ in which $R^Z$ is $(CH_3)_3$—; and
$R^2$ is $CH_3C(O)O$—, and
b) the epidermal growth factor receptor antibody, cetuximab,
in which the active ingredients are present in each case in free form or as a pharmaceutically acceptable salt, solvate or ester.

6. The method according to claim 5 wherein the taxane is administered orally at a synergistically thereapeutic effective dose of 8 to 320 mg/m² p.o. every 1 to 14 days for 1 or more administrations.

7. The method according to claim 5 wherein cetuximab is administered at a synergistically thereapeutic effective dose of 4 to 400 mg/m². i.v. every 1 to 14 days for 1 or more administrations.

8. The combination according to claim 5 wherein the taxane is administered orally at at a synergistically thereapeutic effective dose of 8 to 320 mg/m² p.o. every 1 to 14 days for 1 or more administrations and cetuximab is administered at a synergistically thereapeutic effective dose of 4 to 400 mg/m². i.v. every 1 to 14 days for 1 or more administrations.

9. The method according to claim 5 wherein the cancer treated is selected from colorectal cancer, breast cancer, gastric cancer, ovarian cancer, non-small cell lung cancer and cancers of the head and neck.

* * * * *

UNITED STATES PATENT AND TRADEMARK OFFICE
CERTIFICATE OF CORRECTION

PATENT NO. : 7,132,554 B2
APPLICATION NO. : 11/079064
DATED : November 7, 2006
INVENTOR(S) : Rose It is certified that error appears in the above-identified patent and that said Letters Patent is hereby corrected as shown below:

On the Title Page, Item (74), delete "Elliot" and insert -- Elliott --

In Column 4, line 45, delete "thereapeutic" and insert --therapeutic --

In Column 4, line 48, delete "thereapeutic" and insert --therapeutic --

In Column 10, line 39, delete "ted" and insert -- tert --

In Column 10, line 48, delete "thereapeutic" and insert --therapeutic --

In Column 10, line 52, delete "thereapeutic" and insert --therapeutic --

In Column 10, lines 56-57, delete "thereapeutic" and insert --therapeutic --

In Column 10, line 57, delete "mg/$^2$ p.o." and insert -- mg/m$^2$ p.o. --

In Column 10, line 59, delete "thereapeutic" and insert --therapeutic --

In Column 11, line 16, delete "ted" and insert -- tert --

In Column 11, line 17, delete "(CH$_3$)$_3$-;" and insert -- (CH$_3$)$_3$CO-; --

In Column 12, line 2, delete "thereapeutic" and insert --therapeutic --

In Column 12, line 6, delete "thereapeutic" and insert --therapeutic --

In Column 12, line 7, delete "mg/m$^2$. i.v." and insert -- mg/m$^2$ i.v.--

In Column 12, lines 10-11, delete "thereapeutic" and insert --therapeutic --

In Column 12, line 13, delete "thereapeutic" and insert --therapeutic --

UNITED STATES PATENT AND TRADEMARK OFFICE
CERTIFICATE OF CORRECTION

PATENT NO.        : 7,132,554 B2
APPLICATION NO.   : 11/079064
DATED             : November 7, 2006
INVENTOR(S)       : Rose It is certified that error appears in the above-identified patent and that said Letters Patent is hereby corrected as shown below:

In Column 12, line 14, delete "mg/m$^2$. i.v." and insert -- mg/m$^2$ i.v.--

Signed and Sealed this

Eighteenth Day of September, 2007

JON W. DUDAS
*Director of the United States Patent and Trademark Office*